US00PP09028P

United States Patent [19]

Hoff

[11] Patent Number: Plant 9,028

[45] Date of Patent: Jan. 3, 1995

[54] VARIETY OF LILIUM NAMED FÜR ELISE

[75] Inventor: Petrus M. M. Hoff, Steenbergen, Netherlands

[73] Assignee: Hoffgaarde B.V., Steenbergen, Netherlands

[21] Appl. No.: 177,195

[22] Filed: Jan. 4, 1994

[51] Int. Cl.[6] ..... A01H 5/00
[52] U.S. Cl. ..... Plt./87.4
[58] Field of Search ..... Plt. 87.4

*Primary Examiner*—James R. Feyrer
*Attorney, Agent, or Firm*—Webb Ziesenheim Bruening Logsdon Orkin & Hanson

[57] ABSTRACT

A new and distinct cultivar of lily plant named Für Elise, particularly characterized by red upper surfaces and yellow to yellowish-white lower surfaces of the flowers, height of about 100 cm, pedicel 10–12 cm long with 3–5 flowers, small leaves, and capable of producing stems and flowers for cut-flower production.

1 Drawing Sheet

BACKGROUND OF THE INVENTION

The present invention comprises a new and distinct cultivar of lily, botanically known as Lilium asiatic and hereinafter referred to by the cultivar name Für Elise.

The new cultivar is a product of a planned breeding program which had the objectives of creating new lily cultivars with the capacity to produce stems and flowers for cut-flower production.

The new cultivar was originated from a hybridization made by the inventor Messr. Petrus Mattheus Maria Hoff in a controlled breeding program at Hoffgaarde, B.V., Franseweg 9, 4651 PV Steenbergen, The Netherlands in 1989. The female and male parents were seedlings originated by Applicant, which were proprietary, and maintained by Applicant for breeding purposes.

The new cultivar was discovered and selected as one flowering plant within the progeny of the stated cross by the inventor on May 15, 1991 in a controlled environment in Steenbergen.

The first act of asexual reproduction of the new cultivar was accomplished by the inventor when scales were taken from the initial selection on Sep. 20, 1991 in a controlled environment in Steenbergen.

Horticultural examination of selected units initiated Mar. 25, 1992 has demonstrated that the combination of characteristics as herein disclosed for the new cultivar are firmly fixed and are retained through successive generations of asexual reproduction.

The new cultivar has not been observed under all possible environmental conditions. The phenotype may vary significantly with variations in environment such as temperature, light, intensity, and day length. The following observations, measurements, and comparisons describe plants grown in Steenbergen under greenhouse conditions which approximate those generally used in commercial practice.

The following traits have been repeatedly observed and are determined to be basic characteristics of the new cultivar which in combination distinguish this lily as a new and distinct cultivar.

1) Flower color having an interesting white-blushed-with-red character, with tepals having an essentially white ground color centerally, with soft but progressively more intensive red blush with progressive proximity to the margin and apex of each tepal.

2) About 100 cm in height.

3) Pedicel 10–12 cm in length with 3–5 flowers.

4) Small leaves.

The accompanying color photographic drawing shows typically flower characteristics of the new cultivar, with colors being as true as possible with illustrations of this type. In the following description, color references are made to The Royal Horticultural Society Colour Chart. The color values were determined at Steenbergen on Mar. 25, 1992.

THE PLANT

Classification:
- *Botanic.*—*Lilium asiatic.*
- *Commercial.*—Hybrid asiatic lily for cut flower production.

Form: Single upright stem from each bulb.
Height: About 100 cm.
Growth habit: Upright, erect, strong and rigorous.
Stem:
- *Diameter.*—1 cm average.
- *Color.*—Yellow-Green Group 146A.
- *Form.*—Rounded.

Foilage:
- *Quantity.* 100–120 leaves.
- *Size of leaf.*—About 9 cm long, 0.8 cm wide up to 12 cm long, 1.5 cm wide.
- *Shape of leaf.*—Elliptic.
- *Texture of leaf.*—Smooth.
- *Color.*—Green Group 137A.

Bulbs:
- *Size.*—12-cm in circumference.
- *Color.*—Pinkish-red and white.

THE BUD

Form: Oblong, rounded ends (UPOV Type II).
Size: 12 cm in length.
Color: Greyed-Red Group 180A.

THE FLOWER

Blooming habit: 80 days after planting.
Size: 22 cm in diameter.
Borne: Compound umbellate.
Shape: B road acute (UPOV Type V).
Tepalage
- *Number of tepals.*—6.

*Arrangement.*—Hexagonal inner tepals spaced apart by about 4 mm at their bases.

*Size.*—12–14 cm long; inner tepals about 6 cm wide; outer tepals about 4 cm wide.

*Color*: (*inner and outer tepals*).—Upper surface: Red Group 54A at the apex, Red Group 54C in the middle, Yellow Group 3A and Yellow-White Group 158B at the base. Lower surface: Yellow Group 3A to Yellow-White Group 158B.

*Spotting.*—None.

Pedicel:

*Reflecting.*—None

*Length.*—12 cm.

*Color.*—Dark green with much anthocyanin coloring.

*Form.*—Upright.

Nectaries

*Size.*—About 2 cm long.

Texture: Smooth.

Disease resistance: No unusual disease problems have been observed.

Fragrance: None.

Lasting quality: 11 days in water after cutting.

REPRODUCTIVE ORGANS

Stamens:

*Number.*—6

*Length.*—8 cm.

*Color.*

*Anthers-color.*—Brown.

*Pollen-color.*—Greyed-Orange Group 171A.

*Filaments-color.*—Pinkish-purple.

Pistils: One, long.

*Color.*—Greyed-Orange Group 174A.

Stigma:

Color.—Dark brown.

Ovaries

*Color.*—Green.

I claim:

1. A new and distinct variety of lily plant substantially as shown and described.

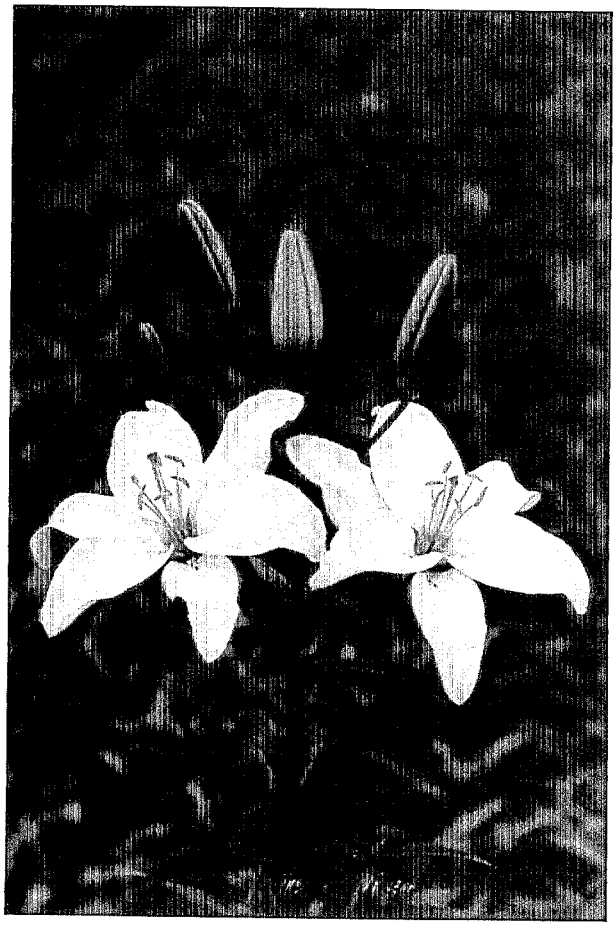

* * * * *